(12) United States Patent
Yang et al.

(10) Patent No.: US 10,500,173 B2
(45) Date of Patent: *Dec. 10, 2019

(54) ANTIMICROBIAL SILICONE-BASED WOUND DRESSINGS

(75) Inventors: Liu Yang, Toronto (CA); Valerio DiTizio, Toronto (CA)

(73) Assignee: COVALON TECHNOLOGIES INC., Mississauga (CA)

( * ) Notice: Subject to any disclaimer, the term of this patent is extended or adjusted under 35 U.S.C. 154(b) by 455 days.

This patent is subject to a terminal disclaimer.

(21) Appl. No.: 13/163,224

(22) Filed: Jun. 17, 2011

(65) Prior Publication Data
US 2011/0313048 A1    Dec. 22, 2011

Related U.S. Application Data

(60) Provisional application No. 61/355,725, filed on Jun. 17, 2010.

(51) Int. Cl.
*A61K 31/195*    (2006.01)
*A61K 31/155*    (2006.01)

(52) U.S. Cl.
CPC .................................. *A61K 31/155* (2013.01)

(58) Field of Classification Search
CPC .............. C07C 279/265; A61K 9/7007; A61K 31/155; A61L 15/16; A61L 15/46; C08G 77/04; C08G 77/045
See application file for complete search history.

(56) References Cited

U.S. PATENT DOCUMENTS

| | | | |
|---|---|---|---|
| 3,439,676 A | 4/1969 | Burda | |
| 4,102,401 A | 7/1978 | Erbstoesser | |
| 5,019,096 A | 5/1991 | Fox, Jr. et al. | |
| 5,102,401 A | 4/1992 | Lambert et al. | |
| 5,451,424 A | 9/1995 | Solomon et al. | |
| 6,572,878 B1 | 6/2003 | Blaine | |
| 2004/0175344 A1 | 9/2004 | Woller | |
| 2004/0175414 A1 | 9/2004 | Berlat | |
| 2009/0035388 A1 | 2/2009 | Dudnik et al. | |
| 2009/0104252 A1 | 4/2009 | Alam et al. | |
| 2010/0292626 A1 | 11/2010 | Gundersen et al. | |

FOREIGN PATENT DOCUMENTS

| | | |
|---|---|---|
| AU | 750719 B2 | 7/2002 |
| CA | 2109720 A1 | 1/1993 |
| CN | 1256709 A | 6/2000 |
| CN | 101394898 A | 3/2009 |
| EP | 0328421 A2 | 8/1989 |
| WO | 2009052193 A1 | 4/2009 |

OTHER PUBLICATIONS

International Search Report and Written Opinion, dated Sep. 16, 2011, in related PCT patent application No. PCT/CA2011/000712.
Lee et al., "Solvent Compatibility of Poly(dimethylsiloxane)-Based Microfluidic Devices", Analytical Chemistry, 2003, vol. 75, No. 23, pp. 6544-6554.
Hu et al, "Controlled release from a composite silicone/hydrogel membrane", ASAIO, 2000, vol. 45, pp. 431-434.
Denadai et al., "Superamolecular self-assembly of b-cyclodextrin: an effective carrier of the antimicrobial agent chlorhexidine", Carbohydrate Research, 2007, vol. 342, pp. 2286-2296.
Extended European Search Report, dated Nov. 13, 2015, in relation to European Application No. 11794995.8, filed on Jan. 17, 2013.
Chinese Patent Office, "Office Communication", dated Dec. 30, 2013, in relation to Chinese Patent Application No. 201180039573.X.
Kantamneni, "Office Communication", dated Sep. 18, 2013, in relation to U.S. Appl. No. 13/599,194.
Kantamneni, "Office Communication", dated Feb. 26, 2013, in relation to U.S. Appl. No. 13/599,194.
Notice of Allowance issued by the Korean Intellectual Property Office (KIPO) dated Mar. 14, 2019, in the corresponding Korean Application No. 10-2013-7001098. (with English Translation).

*Primary Examiner* — Shobha Kantamneni

(57) ABSTRACT

Antimicrobial silicone-based dressings, such as wound dressings, are disclosed. An example dressing comprises a transparent and self-adhesive gel sheet cured from a liquid containing silicone, the sheet having dispersed therein (i) particulates of a chlorhexidine compound that is not soluble in the liquid; and (ii) at least one other antimicrobial. Methods of making the silicone-based dressings and methods of use are also disclosed.

8 Claims, 2 Drawing Sheets

ANTIMICROBIAL SILICONE-BASED WOUND DRESSINGS

CROSS-REFERENCE TO RELATED APPLICATIONS

This application claims the benefit of, and priority from, U.S. provisional application No. 61/356,725 filed on Jun. 17, 2010, the entire contents of which are incorporated herein by reference.

FIELD OF THE INVENTION

The present invention relates to antimicrobial wound dressings. More specifically, the invention relates to antimicrobial silicone-based wound dressings for covering wounds and lesions or the like that further provide visual, strength and adhesive properties. The invention also relates to methods of making the antimicrobial silicone-based wound dressings and methods of use thereof.

BACKGROUND

Dressings play a major role in wound management, since the moist, warm and nutrient-rich environment of typical wound sites provide ideal conditions for microbial growth. Bacterial colonization and subsequent infection can interfere with the wound healing process by producing various substances (e.g., toxins, proteases and pro-inflammatory molecules) capable of inducing excessive and prolonged inflammatory responses of the host tissues.

Antimicrobial dressings are, for example, used for activity against antibiotic-resistant bacteria such as methicillin-resistant Staphylococcus aureus (MRSA), Gram-negative rods, and Candida species. These are the most commonly occurring organisms that cause infections in the use of intravascular and central venous catheters (CVCs) such as intra-venous (IV) catheters, mid-line catheters, dialysis catheters, peripherally-inserted central catheters, chest tubes and so on. Such vascular access catheters are widely used but are associated with catheter-related infection.

Dressings are applied to vascular access sites to minimize the contamination of the insertion site and provide stability of the device. Commercially available intravenous access site dressings (I.V. dressings), such as OpSite® CH (Smith & Nephew, England) or Tegaderm® CHG (3M, USA), include an acrylic-based pressure sensitive adhesive or an adhesive that has similar properties. When repeatedly applied and removed from the same area of the skin surface, e.g. as in the changing of a medical or surgical dressing, or when in place over a prolonged period, such adhesives are apt to remove with them parts of the upper skin layer (the stratum corneum) potentially resulting in skin damage. In addition, these adhesives also fasten strongly to hairs on the skin, often causing pain and discomfort when removing the dressing.

Silicones, as a group, are synthetic polymers containing the recurring group —$SiR_2O$—, wherein R is a radical such as an alky, acyl, phenyl or vinyl group. They are extremely hydrophobic materials with almost no capacity of water uptake, which strongly limits them from fully functioning as a drug releasing wound dressing [Hu et al, Controlled release from a composite silicone/hydrogel membrane, ASAIO 2000; 46: 431-434]. Silicone has been combined with antimicrobial agent(s), such as chlorhexidine digluconate or elemental silver or silver salts. [U.S. Pat. No. 6,572,878; US 2009/0104252].

Due to the properties of silicone, it is difficult to incorporate sufficient amounts of antimicrobial into silicone to achieve a desired antimicrobial activity. Moreover, the amount of antimicrobial used in conjunction with silicone may provide undesirable qualities to the silicone. For example too high an amount of antimicrobial may result in an unworkable and tacky gel or lead to the formation of an opaque gel. All of these characteristics are undesirable.

SUMMARY

A silicone-based dressing, such as a wound dressing, that includes chlorhexidine that is insoluble in the mixture used to form the dressing, resulting in particulates of chlorhexidine dispersed throughout the resulting dressing, is disclosed. The inclusion of chlorhexidine that is insoluble in the mixture allows for a high loading capacity of chlorhexidine into the final dressing.

Surprisingly, the silicone-based dressing may still maintain desired properties such as tackiness, elasticity and transparency, despite the inclusion of the particulate chlorhexidine. In addition to the particulate chlorhexidine, at least one other antimicrobial is included in the dressing. For example, the other antimicrobial may be a chlorhexidine compound that is soluble in the mixture used to form the dressing, which may further increase the final load of chlorhexidine in the dressing. Alternatively, or additionally, the other antimicrobial may be a photo-stabilized silver agent. Photo-stabilization helps prevent discoloration of the final dressing and helps maintain transparency, thus allowing for visualization of a wound without needing to remove the dressing.

Thus, an example antimicrobial silicone-based wound dressing may offer adhesiveness, continuous effective antimicrobial activity up to about 7 days or more. Further, visibility of a wound site or other surgical site may be maintained, as the dressing may maintain its transparency over the time of its use and has adequate cohesive strength.

According to one aspect of the present invention, there is provided a method for making a dressing, comprising mixing together a liquid containing silicone, a chlorhexidine compound that is not soluble in the liquid and at least one other antimicrobial to form a mixture; and molding and curing the mixture to form a transparent and self-adhesive gel sheet.

According to another aspect of the present invention, there is provided a dressing comprising a transparent and self-adhesive gel sheet cured from a liquid containing silicone, the sheet having dispersed therein (i) particulates of a chlorhexidine compound that is not soluble in the liquid; and (ii) at least one other antimicrobial.

According to a further aspect of the present invention, there is provided a method for preventing infection of a wound or incision site, the method comprising applying the dressing described herein to the wound or incision site.

According to a further aspect of the present invention, there is provided a method for treating a wound or incision site, the method comprising applying the dressing described herein to the wound or incision site.

According to a further aspect of the present invention, there is provided a method for quantifying chlorhexidine incorporated in a silicone gel sheet, the method comprising breaking down a matrix of the silicone gel sheet; extracting the chlorhexidine with a solvent with a high dielectric constant or with a base saturated alcohol; and quantifying the chlorhexidine against a chlorhexidine standard.

According to a further aspect of the present invention, there is provided a method for quantifying silver incorporated in a silicone gel sheet, comprising breaking down a matrix of the silicone gel sheet; extracting the silver with an aqueous ammonium hydroxide solution; and quantifying the silver against a silver standard.

Other aspects, features, and embodiments of the present invention will become apparent to those of ordinary skill in the art in view of the following description of specific embodiments of the invention in conjunction with the accompanying figures.

BRIEF DESCRIPTION OF THE DRAWINGS

In the figures which illustrate by way of example only, embodiments of the present invention.

DETAILED DESCRIPTION

Figure 1:
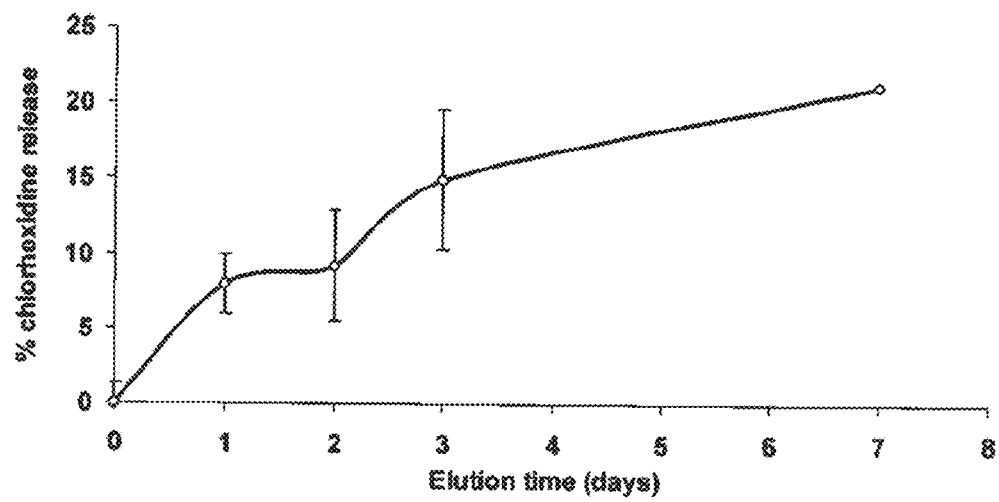
FIG. 1 is a line graph illustrating a gradual release of chlorhexidine salts from a wound dressing according to an embodiment of the invention.

There is provided a dressing comprising a transparent and self-adhesive gel sheet cured from a liquid containing silicone. The gel sheet has dispersed therein (i) particulates of a chlorhexidine compound that is not soluble in the liquid and (ii) at least one other antimicrobial.

An embodiment of the dressing is now described.

The dressing is a silicone-based gel sheet, meaning it is cured from a liquid that contains silicone, i.e. a silicone gel, but comprises additional components.

Silicones are synthetic polymers and take on a variety of forms. In terms of physical properties, at one extreme, there are silicone oils with low melting points, and at the opposite extreme, there are also highly crosslinked silicones which form rigid solids. Intermediate between these two extremes are silicone elastomers, which may take the form of gels, gel sheets or rubbers. Gel sheets comprising silicone elastomers are tacky to the touch, permitting them to adhere to the skin. They are also flexible, therefore allowing them to conform to the contour of a subject's body. Any type of silicone elastomer may be suitable for the dressing disclosed herein. Examples of suitable commercially available silicone gel include, but are not limited to, Dow Corning's soft skin adhesive silicone gel, SILGEL 612™ by Wacker Chemie GmbH, Germany, and MED-6345™ by Nusil Technology.

The liquid that contains the silicone is a pourable mixture. The liquid and silicone mixture may be viscous. It may also contain a solvent such as ethyl acetate or other organic solvent, e.g. dichloromethane, chloroform, cyclopentane, tetrahydrofuran, hexane, cyclohexane, xylene or heptane.

As can be appreciated, upon curing, the liquid containing silicone forms a silicone gel sheet (i.e. a polymeric matrix) as a result of crosslinking between silicone polymer chains. The silicone gel sheet may be soft, durable, washable, and of medical grade. As can be appreciated, the gel sheet provides structural support (i.e. a substrate) to the dressing described herein.

The amount of silicone in the dressing may range from about 95 wt % to about 98 wt %, or from about 96 wt % to about 97 wt %, based on the total weight of the cured dressing.

The dressing includes particulates of a chlorhexidine compound that is not soluble in the liquid containing the silicone.

The word "particulate" means that the chlorhexidine compound is dispersed as fine solid particles in the gel sheet. Such fine solid particles may be visually observable through any suitable microscopic instrument such as an optical microscope or scanning election microscope, or possibly with the naked eye.

Chlorhexidine [1,1-hexamethylene-bis[5-(4-chlorophenyl)-biguanide] is a strong base and practically insoluble in water (0.008% wt/vol at 20° C.). It reacts with acids to form salts with variable solubility in water and is most stable in the form of salts, such as the digluconate, diacetate, and dihydrochloride. Chlorhexidine and its salts are known for their antimicrobial activity against a wide range of Gram-positive and Gram-negative organisms, yeast, fungi, facultative anaerobes, and aerobes [Denadai et aL Superamolecular self-assembly of b-cyclodextrin: an effective carrier of the antimicrobial agent chlorhexidine, Carbohydrate Research 2007; 342: 2286-2296].

Included in the dressing is the chlorhexidine compound that is not soluble in the liquid containing the silicone. As can be appreciated, a chlorhexidine compound is not soluble in the liquid if the chlorhexidine compound is either practically insoluble or slightly soluble in the liquid at ambient temperature. In other words, the chlorhexidine compound remains substantially as solid particles in the liquid at ambient temperature. As will be appreciated, if the chlorhexidine compound is practically insoluble or only slightly soluble in an organic solvent at ambient temperature, the chlorhexidine compound is likely not soluble in the liquid containing the silicone, which can then be readily tested using routine methods.

A suitable chlorhexidine compound that is not soluble in the liquid containing the silicone may be any chlorhexidine compound that exists substantially as a solid at ambient temperature. Examples of such suitable chlorhexidine compounds include, but are not limited to, chlorhexidine free base and its salts such as chlorhexidine diacetate and chlorhexidine dihydrochloride, or any combination thereof. For example, the chlorhexidine compound that is not soluble in the liquid containing the silicone may be chlorhexidine diacetate.

The amount of the chlorhexidine compound that is not soluble in the liquid containing the silicone may range from about 2.0 wt % to 5.0 wt % of the cured dressing. In one case, the amount of chlorhexidine diacetate is about 2.0 wt % of the cured dressing, and in another case, the amount of chlorhexidine diacetate is about 3.0 wt % of the cured dressing.

Also included in the dressing is at least one other antimicrobial. The at least one other antimicrobial may be one or both of chlorhexidine digluconate and a photo-stabilized silver agent.

Chlorhexidine digluconate is hygroscopic and is commercially available as 20% wt/vol aqueous solution. The amount of chlorhexidine digluconate in the dressing may range from about 0 wt % to 1.2 wt % of the cured dressing. In one case, the amount of chlorhexidine digluconate is about 1.0 wt % of the cured dressing.

Silver agents are known to have general antimicrobial properties directed against a wide range of bacteria and fungi. The silver agents may be provided as silver salts. Examples of suitable silver salts include, but are not limited to, silver nitrate, silver acetate, silver lactate and any combination thereof.

The silver agent may be photostabilized to deter photo-induced discoloration using standard techniques known to those skilled in the art. For example, the silver agent may be photostabilized in accordance with a procedure disclosed in U.S. Patent Publication No. 2009/0035388 to Dudnik et al.

Specifically, the silver agent may be photostabilized with (i) a compound containing a basic nitrogen atom to complex with silver as is understood by a skilled person in the art and (ii) a dye.

Suitable compounds containing a basic nitrogen atom includes one or more of ammonia, tris(hydroxymethyl) aminomethane, pyrrolidone carboxylic acid (D,L-pyroglutamic acid), polyethyleneimine, and amino acids. Suitable amino acids include alanine, arginine, asparagine, cysteine, glutamine, glutamate, glycine, histidine, isoleucine, lysine, methionine, phenylalanine, proline, serine, threonine, tryptophan, tyrosine and valine and any combination thereof.

A suitable dye includes any cationic triarylmethane dye such as, but not limited to, Brilliant Green, Malachite Green, Methylene Blue, Ethyl Violet, Crystal Violet, Victoria Blue R, Victoria Blue B and Victoria Pure Blue BO and any combination thereof. Suitable dyes may be commercially available from Sigma-Aldrich, U.S.A.

Complexing silver with the compound containing a basic nitrogen atom may prevent the silver from subsequent oxidation/reduction reactions that would lead to discoloration of the silver. The dye may also protect the silver from subsequent reduction reactions that would cause color changes in the silver.

The total amount of silver agent present in the dressing may range from about 0.025 wt % to about 0.5 wt % of the cured dressing.

In one case, D,L-pryoglutamic acid and Brilliant Green may be used to stabilize a silver agent, such as silver acetate. The total amount of silver acetate present in the dressing is about 0.025% by weight.

Thus, in one embodiment, the transparent and self-adhesive gel sheet cured from a liquid containing silicone has dispersed therein (i) particulates of a chlorhexidine compound that is not soluble in the liquid and (ii) chlorhexidine digluconate.

In a further embodiment, the gel sheet has dispersed therein (i) particulates of a chlorhexidine compound that is not soluble in a liquid containing silicone and (ii) a photo-stabilized silver agent.

In yet another embodiment, the gel sheet has dispersed therein (i) particulates of a chlorhexidine compound that is not soluble in a liquid containing silicone, (ii) chlorhexidine digluconate and (iii) a photo-stabilized silver agent.

In the above embodiments, the chlorhexidine compound that is not soluble in the liquid containing silicone may be chlorhexidine diacetate.

The dressing may be self-adhesive and transparent. As can be understood, adhesive or self-adhesive means that the dressing may adhere onto another surface without the use of any additional substance such as a glue or paste. The dressing may also be sufficiently transparent such that a wound covered by the dressing may be viewed through the dressing in order to monitor healing and treatment progress of microbial contamination. Further, the dressing may also be cohesively strong, in other words, the dressing may be applied to a surface and subsequently removed with no or minimum residue left, possibly due to sufficiently strong intermolecular bonding (i.e. crosslinking) between silicone polymer chains.

As can be appreciated, the chlorhexidine compound that is not soluble in the liquid containing the silicone, for example, chlorhexidine diacetate powder, may be evenly distributed within the silicone gel sheet without impacting on the transparency and tackiness of the silicone gel and may help to provide a consistent antimicrobial effect over time. In other words, the chlorhexidine compound may inhibit microbial growth at wound sites, while simultaneously minimizing the impact on the cohesive strength and transparency of the dressing. The chlorhexidine digluconate and/or photo-stabilized silver agent may help to achieve a desirable level of antimicrobial activity due to an increased amount of the total antimicrobial agents.

Cohesive strength of the silicone gel sheet may be maintained when no more than about 5% (wt %) total chlorhexidine (including the chlorhexidine compound, and chlorhexidine digluconate if incorporated in the gel sheet) is added to the silicone. The total amount of chlorhexidine in the dressing may be from about 2.0 wt % to about 5.0 wt %, or may be, in some embodiments ≤2 wt %, meaning wt % based on the weight of the cured dressing.

The dressing described herein may provide a gradual release of the chlorhexidine compound and the at least one other antimicrobial to inhibit microbial growth for about 7 days or more, while still allowing the dressing to remain transparent (for direct visualization of wounds) and also remain cohesively strong.

The thickness and weight of the dressing may vary according to the particular application in which it is to be used and the moisture vapor transmission rate required in that application. Typically, the thickness may vary from tens of microns up to several millimeters (mm) such as 0.05 mm to 3.0 mm. For example, if the dressing is applied to a vascular access puncture site, a thin dressing may be utilized. Such a thin layer may be from about 50 to 200 microns, in aspects from about 100 to 150 microns.

The dressing may also be coated on a non-adhesive breathable backing using any suitable method known in the art. Suitable non-adhesive breathable backing layer includes a conventional non-woven fabric, woven fabric knit, paper or synthetic film (e.g. polyvinyl chloride film, polyurethane film) and the like. The non-adhesive breathable backing layer has a moisture vapor transmission rate of at least 1,000 $g/m^2/d$, or at least 1,500 $g/m^2/d$. When coated with a non-adhesive breathable backing layer, the dressing may not cause maceration of healthy skin to which it may be applied since the dressing is moisture vapor permeable with a moisture vapor transmission rate greater than that of normal healthy skin, i.e. 204±12 $g/m^2/d$.

A release liner made of a non-silicone material, such as polycarbonate, polyethylene, or wax paper, may be used to cover and protect the dressing prior to applying the dressing.

The dressing may be provided in sterilized form, and may be kept in a sterile package such as a paper/paper, paper/plastic, Tyvek®/plastic, or Tyvek®/Tyvek® pouches. Sterilization may be achieved in a conventional manner, e.g. heat or ethylene oxide. During use, the sterile dressing is removed from the pouch, the release liner is removed from the adhesive surface of the dressing and the dressing is applied to the wound or onto a catheter or other desired surface.

Thus, the dressing described herein is useful for medical applications to treat a wound site or other surgical site such as an incision site, to dress the wound or site, and also in some cases to prevent infection of the wound or site.

Therefore, the dressing may be used to dress or treat a wound, to prevent infection of a wound or other site such as an intravenous access site.

The dressing is applied as an I.V. dressing, a wound dressing, a wound barrier, a strip, a first aid bandage or a surgical drape. In general, the dressing may be used in any medical wound application to reduce potential microbial contamination. It may also be used in therapeutic drug, medicament and/or chemical agent delivery.

As used herein, preventing infection of a wound or other incision site refers to an approach for obtaining beneficial or desired results, including clinical results. Such beneficial or desired results include, but are not limited to, reducing the risk of infection, minimizing an infection, reversing an infection, preventing any infecting microbe from growing, halting any infection from occurring, preventing any infection from spreading or increasing, slowing or reducing an existing infection.

The infection may be any infection likely to occur at a wound or incision site, for example a bacterial, viral, parasitic or fungal infection.

The dressing may be used as a coating or film and may be trimmed to any desired shape and size for medical applications, such as wound dressings, surgical drapes, medical tapes, strips, bandages, first aid dressings, IV dressings for securing a catheter or cannula to reduce the risk of infection at the injection site. Therefore, the dressing may be provided as an I.V. dressing, a wound dressing, a wound barrier, a strip, a first aid bandage or a surgical drape.

A method for making the dressing is disclosed.

In one embodiment, the chlorhexidine compound that is not soluble in the liquid containing the silicone, the silver agent and the photo-stabilizing agents are mixed in the liquid containing the silicone to form a mixture.

The mixture is molded to a desired shape and thickness, and then cured under suitable conditions of temperature and pressure, in the presence or absence of a catalyst, to form a transparent and self-adhesive gel sheet. If a catalyst is used, the catalyst may be platinum. Curing times, temperatures and pressures for forming the gel sheet are known in the art.

In some cases, chlorhexidine digluconate, which may be provided as 20% wt/vol aqueous solution, may be added to the mixture. Chlorhexidine digluconate may act as a solvent for the chlorhexidine compound. The ratio of the chlorhexidine compound: 20% wt/vol chlorhexidine digluconate solution may be about 2:1 based on final solid wt % in the cured dressing.

The mixing may be achieved by any standard mechanical means such as stirring, blending or agitation. The ingredients may be mixed together or added in order to form the mixture.

In some cases, before mixing with the liquid containing the silicone, the chlorhexidine compound may be first blended with the silver compound, the photo-stabilizing agents and 20% wt/vol chlorhexidine digluconate solution, if it is used. The blending may be achieved by any standard mechanical means such as stirring, blending or agitation. Again, the ingredients may be blended together or added one by one for the blending.

The molding may be achieved by pouring the mixture into a mold of the desired shape and/or spreading the mixture to a desired thickness.

The curing (i.e. toughening or hardening of silicone by cross-linking of silicone polymer chains) may be achieved by any suitable method known in the art, such as by heat, chemical additives, ultraviolet radiation or electron beam. The skilled person may also readily determine the suitable conditions of temperature and pressure to be used for the curing, depending on the composition of the mixture and method used for curing. For example, the curing temperature may be from about 100° C. to about 150° C.

A method for quantifying chlorhexidine incorporated in a silicone gel sheet is disclosed. Such a quantification method may be used for quality control purposes.

Even though it is possible to measure the chlorhexidine content in an elution solution, such as water, phosphate buffer saline, or normal saline solution, for example by using a UV/Vis spectrometer, there have been no reports of a method to quantify the actual chlorhexidine amount incorporated in a silicone gel sheet due to the difficulty of extracting chlorhexidine from such an extremely hydrophobic material.

In order to break down (i.e. open up) the silicone gel matrix to allow the exposure and extraction of the chlorhexidine components, organic solvents with low dielectric constants may be used. Examples of such suitable organic solvents include, but are not limited to, dichloromethane, chloroform, cyclopentane, tetrahydrofuran, hexane, cyclohexane, xylene, and heptane.

The organic solvent is added to the silicone gel sheet with the chlorhexidine incorporated therein, for example, at a ratio of about 800-150:1 (vol:wt), or about 125-100:1 and the mixture is stirred from 1 to 5 hours, or from 2 to 3 hours at room temperature in order to break the crosslinked silicone network.

The extraction and dissolution of the chlorhexidine may be carried out by any standard method known in the art. For example, the extraction and dissolution of the chlorhexidine may be carried out by adding and mixing with the same volume of an extracting solvent with a high dielectric constant for about 2 to 5 hours, or about 2.5 to 3 hours. Such extracting solvents include, but are not limited to, denatured ethanol, methanol, and isopropyl alcohol. The resulting extraction mixture is allowed to stand still until a clear supernatant containing chlorhexidine is obtained.

The amount of chlorhexidine contained in the clear supernatant is then determined, for example using an UV/Vis spectrometer in combination with a suitable chlorhexidine standard of known concentration. The chlorhexidine standard may be readily prepared by any standard methods known in the art. For example, the chlorhexidine standard may comprise chlorhexidine diacetate only or a mixture of chlorhexidine salts when more than one form of chlorhexidine is present in the silicone gel sheet.

The chlorhexidine incorporated silicone gel sheet may also be chemically extracted and dissolved in a base (e.g. KOH) saturated alcohol (e.g. isopropyl alcohol).

In a similar manner, the silver content incorporated within the silicone gel sheet may also be quantified.

For example, the silicone gel sheet may be soaked in an organic solvent with a low dielectric constant, for example dichloromethane, chloroform, cyclopentane, tetrahydrofuran, hexane, cyclohexane, xylene, and heptane.

The organic solvent is added to the silicone gel sheet containing the silver at a ratio of about 1:20-100 (wt:vol), or about 1:60-80 and is stirred, for example, from about 30 minutes to about 2 hours, or from about 45 minutes to about 1.5 hours at room temperature to break down the crosslinked silicone network. A base (e.g. KOH) saturated alcohol (e.g. isopropyl alcohol) is added at the same volume of the organic solvent and stirred, for example, from about 30 minutes to about 2 hours, or from about 45 minutes to about 1.5 hours at room temperature to chemically break down the crosslinked silicone network and release the silver content.

The extraction and dissolution of silver compound may be executed by adding and mixing of ammonia hydroxide aqueous solution for about 30 minutes to about 2 hours, or for about 45 minutes to about 1.5 hours at room temperature. The concentration of ammonium hydroxide solution may range from about 2% to about 10%, or from about 4.5% to about 7%. The volume of the ammonium hydroxide solution may be about one to 8 fold, or about 4 to 7 fold, of the total volume of the organic solvent used to break down the crosslinked silicone network. The resulting extraction mixture is allowed to stand still until a clear supernatant containing silver is obtained.

The silver content contained in the clear supernatant is then analyzed, for example using an atomic absorption spectrometer, in combination with a suitable silver standard of known concentration. The silver standard may be readily prepared by any standard methods known in the art.

The present invention is further exemplified below by examples in accordance with embodiments of the invention. In the following examples and throughout this application, all parts and percentages are by weight unless otherwise indicated, and all temperatures are reported in degrees Celsius, unless otherwise specified. Data are reported with mean±standard deviation.

EXAMPLES

Example 1—Preparation of a Dressing 0.25 gram silver acetate, 0.19 g DL-Pyroglutamic acid and 0.001 g Brilliant Green were added and dissolved in order in a 200 ml glass beaker filled with 50 g 20% chlorhexidine digluconate solution, followed by the addition of 20 g of chlorhexidine diacetate powder to form a paste-like mixture. The paste-like mixture was then mixed with 969.559 g silicone gel (Dow Corning® MG 7-9850) in a 2 liter polyethylene beaker equipped with a mechanical stirrer until a homogeneous suspension was achieved. The suspension was spread between a polyurethane sheet and a polycarbonate sheet, cured at a temperature between 100° C. and 120° C. The final concentration (i.e. amount) of chlorhexidine diacetate, chlorhexidine digluconate, silver acetate, DL-Pyroglutamic acid and Brilliant Green in one dressing prepared according to Example 1 was listed below.

| Ingredient | Quantity % |
| --- | --- |
| Chlorhexidine diacetate | 2.0000 |
| Chlorhexidine digluconate | 1.0000 |
| Silver acetate | 0.0250 |
| DL-Pyroglutamic acid | 0.0190 |
| Brilliant Green | 0.0001 |

The gel sheet sandwiched between the polyurethane and polycarbonate films was slightly hazy, but transparent, and soft. It exhibited excellent color stability and transparency over 7 days.

The dressing may be cut into a 4 cm×4 cm square with a cross-slit near the center for use as an IV protective dressing to cover and protect a catheter exit site, or 10 cm×12 cm solid sheet without a slit for use as a catheter securement device or a dressing for minor wounds. The dressing may be packaged in a Tyvek® on Tyvek® pouch and sterilized using ethylene oxide gas.

Figure 3A:
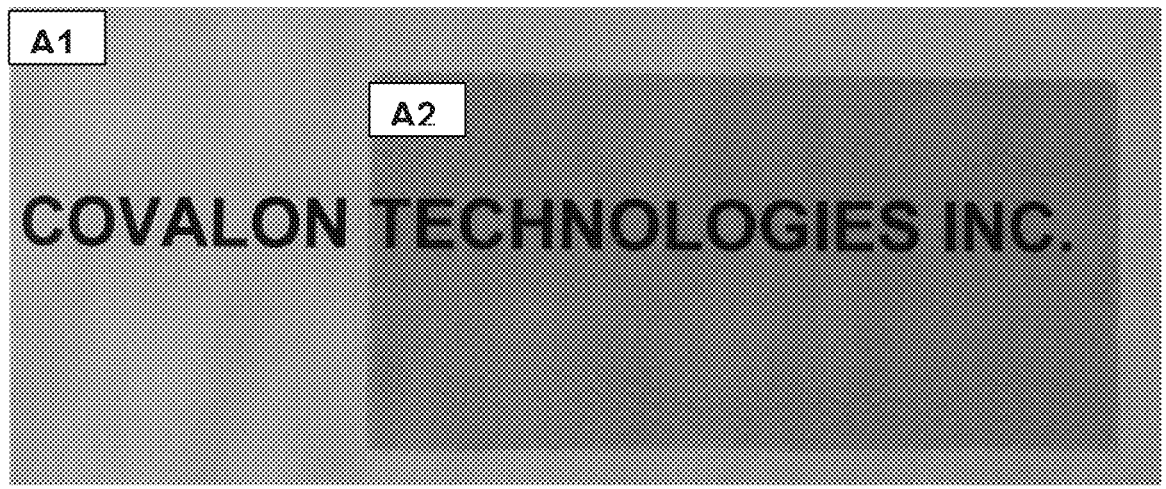
FIG. 3A is an image showing the transparency of a dressing exemplary of an embodiment of the invention, the dressing being used to secure a catheter.

FIG. 3A is an image showing the transparency of a dressing made in accordance with Example 1. Region (A1) shows a portion (the word "COVALON") of a print-out without the dressing being placed over the print-out. Region (A2) shows the transparency of the dressing which was placed over another portion (the words "TECHNOLOGIES INC.") of the print-out. The dressing of FIG. 3A may be used to secure a catheter.

Figure 3B:
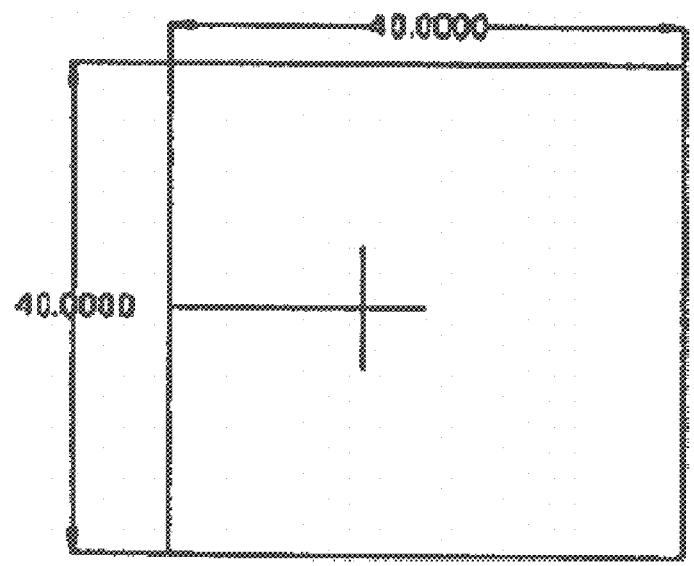
FIG. 3B is a schematic drawing of the dressing depicted in FIG. 3A.

FIG. 3B is a schematic drawing of the dressing depicted in FIG. 3A. It shows that the gel sheet is cut into a 4 cm×4 cm square with a cross-slit near the center for use to secure a catheter.

Example 2—Chlorhexidine Release Profile

Gradual release of chlorhexidine from a dressing described herein is particularly important and applicable when employing such a dressing as a protective barrier to prevent microbial infection. A 4 cm×4 cm dressing made in accordance with Example 1 was incubated in 20 mL of phosphate buffered saline (PBS; pH 7.2) at 37° C. and transferred to the equivalent amount of fresh PBS medium every day until 7 days elapsed. A series of chlorhexidine standard solutions for this kinetic study were prepared in PBS, which contain total chlorhexidine contents at 1.347, 5.389, 10.778, 21.555, 32.333, and 43.110 nanomol/ml. The determination of $\lambda_{max}$ for chlorhexidine in PBS and calibration of chlorhexidine concentration vs. optical density was performed. The chlorhexidine content in the collected PBS solution was analyzed immediately using an UV/Vis spectrometer (Perkin Elmer-Lambda Bio). FIG. 1 shows a constant and slow chlorhexidine release over the 7 days of incubation.

Example 3—Silver Release Profile

Figure 2:
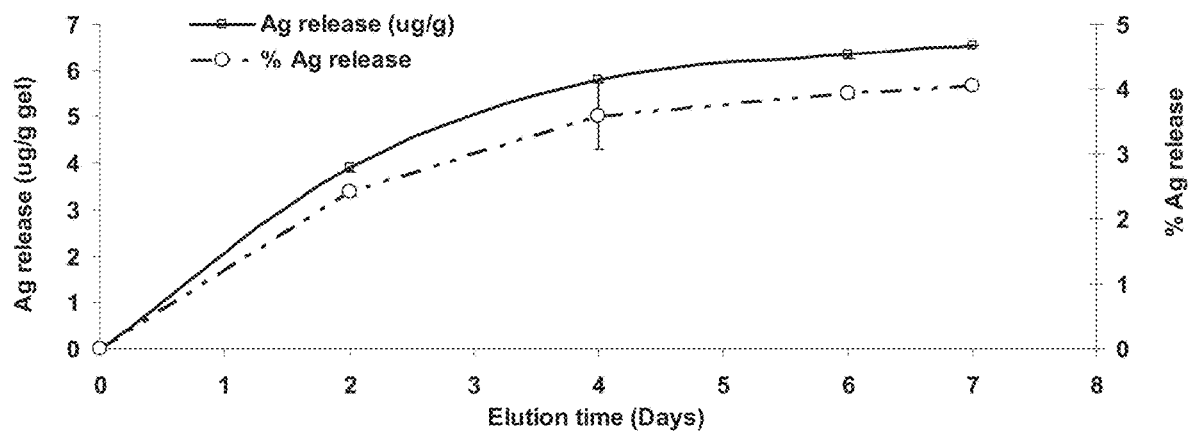
FIG. 2 is a line graph illustrating a gradual release of silver components from a wound dressing according to an embodiment of the invention.

The kinetics of silver release from a dressing made in accordance with Example 1 was also determined. A 4 cm×4 cm dressing made in accordance with Example 1 was incubated in 20 mL of phosphate buffered saline (PBS; pH 7.2) at 37° C. and transferred to the equivalent amount of fresh PBS medium every other day until 7 days. The silver content in the collected PBS solution was analyzed immediately using an atomic absorption spectrometer (Varian SpectrAA-50). FIG. 2 shows a constant and slow silver release over the 7 days of incubation. Both Ag release % and Ag release μg/g were calculated by comparing the silver content measured in the elution solution with the total amount of silver content present in the silicone based dressing that was eluted.

Example 4—Antimicrobial Activity Testing

The antimicrobial activity of a dressing made in accordance with Example 1 was examined using a microbial log reduction test. The polyurethane backing and polycarbonate liner of each sample dressing about 2 cm×2 cm was wiped with 70% isopropanol and left to dry in a biosafety cabinet. After the polycarbonate liner was peeled off, the samples were placed directly onto the Mueller Hinton Agar plates with the adhesive side in contact with the agar and incubated for 3, 5 and 7 days at 36±1° C., in order to mimic the release of antimicrobial agents from the gel when applied onto the skin. Upon completion of each designated period of incubation, samples were transferred to 6-well plates where the polyurethane side of each sample was glued onto the bottom of a well through a piece of double-sided adhesive foam. The adhesive side of each sample was loaded with 200 µl of inoculum containing at least 1×10⁶ CFU and incubated at 36±1° C. for 24 h. The microbial density of the inoculum was measured by the viable plate count method and expressed in log format. The reduction of the initial inoculum was calculated and expressed as the logarithm ($Log_{10}$) of the difference between the initially loaded inoculum and the number of microorganisms remaining in each sample well. The same volume of inoculum was dispensed into a 1.8 ml eppendorff tube as a blank for this test. Silicone gel samples that do not contain antimicrobial agents were used as controls in this study. Five microbial organisms that are frequently associated with medical device-related infections were used in this study. All test articles were prepared in quadruplicate. The results shown in Table 1 demonstrate that the dressing made in accordance with Example 1 consistently offers effective antimicrobial activity for over 7 days.

TABLE 1

Antimicrobial Activity of Dressing over 7 Days

| Micro-organisms | Sources | Antimicrobial Results | | |
|---|---|---|---|---|
| | | Day 3 | Day 5 | Day 7 |
| C. albicans | ATCC 10231 | 4.70 ± 0.03 | 4.26 ± 0.06 | 4.26 ± 0.06 |
| VRE | ATCC 51575 | 5.24 ± 0.03 | 5.77 ± 0.01 | 5.77 ± 0.01 |
| P. aeruginosa | ATCC 9027 | 3.80 ± 0.02 | 4.79 ± 0.01 | 4.79 ± 0.01 |
| MRSA | ATCC 33591 | 5.27 ± 0.03 | 5.54 ± 0.13 | 5.54 ± 0.13 |
| S. epidermidis | Clinical isolate obtained from the Center for Infections and Biomaterials Research at the Hospital for Sick Kids (Toronto, ON). | 6.12 ± 0.03 | 5.14 ± 0.04 | 5.14 ± 0.04 |

Notes:
C. albicans—Candida albicans;
VRE—Vancomycin-resistant Enterococcus
P. aeruginosa—Pseudomonas aeruginosa;
MRSA—Methicillin-resistant Staphylococcus aureus Conveniently, the methods described herein may provide a simplified and cost efficient procedure (e.g. excluding the use of any organic solvents or a hydrophilic enhancer, or excessive amounts of chlorhexidine salts) for manufacturing wound dressings with self-adhesiveness, transparency and antimicrobial activity. Further, the dressings described herein may be biocompatible and provide continuous antimicrobial activity in biological environments such as wound sites resulting from trauma or catheter punctures.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

As used in this specification and the appended claims, the singular forms "a", "an" and "the" include plural reference unless the context clearly dictates otherwise. As used in this specification and the appended claims, the terms "comprise", "comprising", "comprises" and other forms of these terms are intended in the non-limiting inclusive sense, that is, to include particular recited elements or components without excluding any other element or component. Unless defined otherwise all technical and scientific terms used herein have the same meaning as commonly understood to one of ordinary skill in the art to which this invention belongs.

All lists and/or ranges provided herein are intended to include any sub-list and/or narrower range falling within the recited list and/or range.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A dressing consisting of a transparent and self-adhesive gel sheet cured from a liquid containing silicone and formed for adhesion to a wound site or surgical site on a patient, the cured gel sheet formed of a crosslinked silicone elastomer having sufficient crosslinking between silicone polymer chains so that the gel sheet is cohesively strong thereby allowing for application and subsequent removal from the wound site or surgical site while leaving substantially no residue, the cured gel sheet having from 95 wt % to 98 wt % of the crosslinked silicone elastomer and having evenly dispersed throughout the crosslinked silicone elastomer (i) solid particulates of chlorhexidine diacetate that is not soluble in said liquid, at a concentration so as not to disrupt the crosslinking between silicone polymer chains and the self-adhesiveness and cohesive strength of the gel sheet; and (ii) chlorhexidine digluconate, and a silver agent, the silver agent photo-stabilized with a compound containing a basic nitrogen atom to complex with the silver and a dye; the total amount of chlorhexidine present in the cured gel sheet being from 2 wt % to 5 wt %, and the amount of the silver agent present in the cured gel sheet being from 0.025 wt % to 0.5 wt %.

2. The dressing of claim 1, wherein said photo-stabilized silver agent is silver nitrate, silver acetate or silver lactate, or any combination thereof.

3. The dressing of claim 1, wherein said compound containing a basic nitrogen atom is D,L-pyroglutamic acid.

4. The dressing of claim 3, wherein said dye is Brilliant Green, Malachite Green, Methylene Blue, Ethyl Violet, Crystal Violet, Victoria Blue R, Victoria Blue B or Victoria Pure Blue BO, or any combination thereof.

5. The dressing of claim 3, wherein said dye is Brilliant Green.

6. The dressing of claim 1, wherein said dressing is provided as an I.V. dressing, a wound dressing, a wound barrier, a strip, a first aid bandage or a surgical drape.

7. The dressing of claim 1, wherein said dressing has a thickness of up to about 5 mm.

8. A dressing consisting of
(a) a transparent and self-adhesive gel sheet cured from a liquid containing silicone and formed for adhesion to a wound site or surgical site on a patient, the cured gel sheet formed of a crosslinked silicone elastomer having sufficient crosslinking between silicone polymer chains so that the gel sheet is cohesively strong thereby allowing for application and subsequent removal from the wound site or surgical site while leaving substantially no residue, the cured gel sheet having from 95 wt % to 98 wt % of the crosslinked silicone elastomer and having evenly dispersed throughout the crosslinked silicone elastomer (i) solid particulates of chlorhexidine diacetate that is not soluble in said liquid, at a concentration so as not to disrupt the crosslinking between silicone polymer chains and the self-adhesiveness and cohesive strength of the gel sheet; and (ii) chlorhexidine digluconate, and a silver agent, the silver agent photo-stabilized with a compound containing a basic nitrogen atom to complex with the silver and a dye; the total amount of chlorhexidine present in the cured gel sheet being from 2 wt % to 5 wt %, and the amount of the silver agent present in the cured gel sheet being from 0.025 wt % to 0.5 wt %; and (b) a non-adhesive, moisture vapor permeable backing layer layered on a bottom surface of the cured gel sheet, the top surface of the cured gel sheet being able to adhere to the skin of a subject without any additional adhesive.

\* \* \* \* \*